United States Patent [19]

Jackson et al.

[11] Patent Number: 5,696,310

[45] Date of Patent: Dec. 9, 1997

[54] PURIFICATION OF 1,1,1,3,3-PENTAFLUOROPROPANE

[76] Inventors: Andrew Jackson, 9938 W. Mohawk Ave., Baton Rouge, La. 70810; Randolph Kenneth Belter, 14400 Williams Rd., Zachary, La. 70971

[21] Appl. No.: 629,933

[22] Filed: Apr. 12, 1996

[51] Int. Cl.[6] .................................................. C07C 19/38
[52] U.S. Cl. .................................. 570/177; 570/178
[58] Field of Search .................................. 570/177, 178

[56] References Cited

U.S. PATENT DOCUMENTS

| | | | |
|---|---|---|---|
| 4,766,261 | 8/1988 | Bierl | 570/178 |
| 5,475,169 | 12/1995 | Hopp et al. | 570/178 |

*Primary Examiner*—Alan Siegel
*Attorney, Agent, or Firm*—Richard J. Hammond

[57] ABSTRACT

A process for producing a substantially pure polyfluorinated aliphatic hydrocarbon from a crude reaction solution thereof containing unsaturated hydrocarbon and halogenated saturated and unsaturated aliphatic hydrocarbon impurities is disclosed. The process comprises, as a first step, treating said crude reaction solution with a dehydrohalogenation agent that does not substantially react with the polyfluorinated aliphatic hydrocarbon. The treatment converts the halogenated aliphatic impurities into olefinic impurities.

As a second step to the process of this invention, the solution formed from the first step is further treated with an agent that transforms the olefinic hydrocarbon impurities into compounds that have a boiling point than the desired polyfluorinated aliphatic hydrocarbon. The transformed impurities are then separated from the polyfluorinated aliphatic hydrocarbon.

10 Claims, No Drawings

PURIFICATION OF 1,1,1,3,3-PENTAFLUOROPROPANE

FIELD OF THE INVENTION

The present invention relates to a method of purifying polyfluorinated hydrocarbons by the removal of halogenated impurities. More particularly, this invention relates to a method for purifying 1,1,1,3,3-pentafluoropropane (HFC-245fa) by the removal of both unsaturated and saturated chlorinated, iodinated and/or brominated aliphatic compounds.

BACKGROUND OF THE INVENTION

The compound 1,1,1,3,3-pentafluoropropane, sometimes referred to by the designation of HFC-245fa, is presently used to replace 1,1-dichloro-1-fluoroethane as a foam blowing agent. It is also employed in various solvent applications. Accordingly, its commercial manufacture is of great importance.

Various chemical methods have been disclosed for synthesizing HFC-245fa. For example, WO 95/04021 describes a process for preparing hydrofluorocarbons of the formulas $CF_3(CH_2CF_2)_nF$ comprising reacting at least one reactant selected from $CCl_3(CH_2CCl_2)_nCl$, $CCl_3(CH_2CF_2)_nCl$ or $CCl_2[(CH_2CF_2)Cl]_2$, where n=1 to 3, with hydrogen fluoride at a temperature of from about 25° to about 200° C.

U.S. Pat. No. 2,942,036 discloses the formation of HFC-245fa from the hydrogenation of 1,2,2-trichloropentafluoropropane.

In the production of 1,1,1,3,3-pentafluoropropane various impurities are formed which can not be easily separated by conventional physical methods of separation. Therefore, methods of efficiently removing impurities from solutions of 1,1,1,3,3-pentafluoropropane are desirable.

Numerous chemical methods have been proposed for removing unsaturated impurities from saturated hydrohalofluorocarbons. For example, European patent 39311839 (1989) discloses the purification of saturated fluorohalocarbon containing unsaturated impurities by the use of metal oxides to oxidize the unsaturated impurities to carbon dioxide.

In a related disclosure, U.S. Pat. No. 4,034,049 discloses meso-1,2,3,4-tetrachlorobutane produced in an improved liquid phase chlorination process wherein the trans-1,4-dichlorobut-2-ene is contacted with chlorine in the presence of a catalytic amount of molybdenum.

SUMMARY OF THE INVENTION

A process for purifying polyfluorinated aliphatic hydrocarbons, such as HFC-245fa is provided. A solution of the impure (crude) polyfluorinated compound containing both unsaturated as well as saturated and unsaturated halogenated hydrocarbon impurities is treated with an eliminating agent to convert the halogenated impurities to their corresponding olefins. The resulting solution of the crude polyfluoro aliphatic hydrocarbon, is then oxidized or chlorinated which, in turn, transforms both the olefins originally present in the crude mixture as well as those created from the dehydrohalogenation reaction into the corresponding oxygen- or chlorine-containing compounds which have a higher boiling point than the original olefinic and halogenated impurities. These transformed impurities can be easily removed by conventional processes, such as distillation.

DESCRIPTION OF THE PREFERRED EMBODIMENTS

As used herein, by "unsaturated compounds, unsaturated impurities or olefins" is meant any organic compound containing at least one double or triple bond.

The process of the present invention is carried out by first treating a solution of polyfluoro aliphatic hydrocarbon, such as HFC-245fa, which contains in addition to the polyfluoro aliphatic hydrocarbon, smaller amounts of undisirable olefins as well as saturated and unsaturated halogenated hydrocarbon compounds as impurities, with a dehydrohalogenating agent. As a second step, the solution is then oxidized or chlorinated. The resulting solution can then be purified by distillation or other conventional purification procedure.

In the first step of the process of the present invention, a dehydrohalogenating agent is used to convert the various halogenated compounds into their corresponding unsaturated compounds. This step substantially converts any chlorine-, bromine- or iodine-containing impurity into a dehydrochlorinated, dehydrobrominated and or dehydroiodinated reaction product. The dehydrohalogenating agent does not, however, cause the desired polyfluorinated compound to lose hydrogen fluoride. As such, various dehydrohalogenating agents can be used. However one must be careful not to choose agents and conditions that can react with HFC-245fa.

The dehydrohalogenating agents can be compounds, including but not limited to, the alkali metal hydroxides, e.g., potassium hydroxide (KOH) or sodium hydroxide (NaOH) or bicyclic amidines such as 1,5-diazabicyclo [3.4.0] nonene-5 (DBN) or 1,8-diazabicyclo[5.4.0] undecene-7 (DBU). These agents are used in the molar ratios of from about 1:1 to about 1:5, impurity concentration to dehydrohalogenating agent.

When KOH and NaOH are used, water in the amount of 2 to 20% by weight of the crude polyfluorinated aliphatic hydrocarbon solution may be added, optionally along with a phase transfer catalyst in the amount of about 1 to 5 molar % based on the dehydrohalogenating agent.

When DBN and DBU are used, water or the phase transfer catalyst is not needed.

The dehydrohalogenation reactions can be carried out in a temperature range of about 0 to about 100° C. Preferably the dehydrohalogenation is conducted at a temperature range of about 10 to 60° C. However, while these temperatures are provided as guides, any temperature may be used which effectively permits the dehydrohalogenation of the undesirable impurities.

The second step of the process of the present invention requires that the olefinic impurities be treated by reaction with an oxidizing agent or with chlorine.

In the case of using an oxident to carry out the second step, a variety of oxidation agents, including but not limited to potassium permanganate ($KMnO_4$), osmium tetroxide ($OsO_4$) and ruthenium tetroxide ($RuO_4$) are used. These agents are capable of oxidizing unsaturated compounds to provide compounds with boiling points substantially different (and therefore readily separable) from that of the polyfluorinated aliphatic hydrocarbon.

Similar to the first step dehydrohalogenation reaction, this oxidation reaction is carried out in the liquid phase and requires water in the amount of from about 2 to about 20% by weight of the concentration of polyfluorinated compound in the solution. A phase transfer catalyst may optionally be used in the amount of from about 0.1 to about 5 molar % based on the concentration of the oxidizing agent.

The oxidizing agents of this second (oxidation) step, such as $KMnO_4$, $OsO_4$, $RuO_4$ and the like can be used "neat" for liquid phase oxidation or on the surface of metal oxides for solid phase oxidation.

The second step oxidation reaction can be carried out at a temperature ranging from about 0° to about 100° C. and preferably in a temperature range of 10° to 60° C. However, while these temperatures are provided as guides, any temperature may be used which effectively permits oxidation of the unsaturated compounds.

As a further embodiment of the second step of the process of the present invention, the unsaturated compounds may be contacted with a chlorinating agent that provides a source of chlorine, thus chlorinating the dehydrohalogenated, i.e., olefinic impurities. The chlorinating agent is added in an amount sufficient to chlorinate the unsaturated impurities. Chlorine is the preferred chlorinating agent. It is added to the crude polyfluorinated aliphatic hydrocarbon solution at a molar ratio of about 1:1 to about 1.5:1 chlorine to concentration of unsaturated impurities in solution. Chlorine is added in either the gaseous or liquid form.

Although thermal chlorination can be applied to this process, photochlorination is preferred. In the photochlorination process, the chlorine-treated crude mixture is irradiated with a mercury lamp with sufficient wattage capable of inducing the conversion of the unsaturated impurities to their corresponding photochlorination products.

These photochlorination reactions can be carried out at temperatures ranging from about −25° to about 100° C. Preferably the photochlorination is carried out at about −10° to about 25° C. However, while these temperatures are provided as guides, any temperature may be used which effectively permits chlorination of the unsaturated compounds.

As an additional embodiment of the present invention, it is possible to eliminate the dehydrohalogenation step of the process set forth above when there is an abundance of unsaturated hydrocarbon or of unsaturated halogenated hydrocarbon impurity in the crude polyfluorinated aliphatic hydrocarbon solution. In such a case, the second step, e.g., oxidation or chlorination is accomplished without the first dehydrohalogenation treatment. The resulting, transformed unsaturated compounds are, of course, readily removed by conventional processes such as by distillation.

EXPERIMENTAL

EXAMPLE 1

To a chilled 15 ml glass vial was added 5 ml of chilled 98.35% pure HFC-245fa. To this was added 0.1 grams of KOH or DBU, 0.005 grams of tetrabutyl ammonium hydrogen sulfate and 0.4 grams of water. The whole was sealed with a viton septa and shaken for 3 hours. A vapor phase sample was taken and analyzed by glc/ms.

Results of the above analysis show that the chlorinated and brominated compounds such as $CH_2F-CH_2-CHFBr$ and $CF_3-CH_2-CF_2Cl$ were converted to $CH_2F-CH=CHF$ and $CF_3-CH=CF_2$, respectively.

EXAMPLE 2

To the sample in example 1, a slurry containing 0.25 grams of $KMnO_4$ in 0.4 grams of water was added. The sampled was then shaken for 3 hours. A vapor phase sample was taken and analyzed by glc and glc/ms.

Results of the vapor phase analysis show that the olefins were removed and the original purity of 98.35% was increased to 99.35%.

EXAMPLE 3

To a sample as in example 1, a slurry containing 0.25 grams of $RuO_4$ in 0.4 grams of water was added. The sampled was then shaken for 3 hours. A vapor phase sample was taken and analyzed by glc and glc/ms.

Results of the vapor phase analysis show that the olefins were removed and the purity of 96.53% was increased to 98.59%.

EXAMPLE 4

Into a 3000 ml photochlorination apparatus rifled with a dry ice condenser was added 2000 ml of chilled 90.0% pure HFC-245fa. Chlorine gas was bubbled into the mixture until solution became pale yellow. The solution was then irradiated with a 400 watt Hg lamp for 1 hour. The solution was washed of residual chlorine with dilute $NaHSO_3$ solution and dried with $MgSO_4$.

The solution was then distilled giving 1,468 grams of 99.0% pure HFC-245fa.

I claim:

1. A process for producing a substantially pure polyfluorinated aliphatic hydrocarbon from a reaction solution thereof said reaction solution also containing unsaturated as well as unsaturated and saturated halogenated hydrocarbon impurities, said process comprising the steps of
   1) treating said reaction solution with a dehydrohalogenating agent that does not substantially react with said polyfluorinated aliphatic hydrocarbon selected from the group consisting of an alkali metal hydroxide and a bicyclic amidine thereby forming a solution that comprises said polyfluorinated aliphatic hydrocarbon and olefinic hydrocarbon impurities;
   2) reacting the solution of Step 1 with an agent that converts said olefinic hydrocarbon impurities to compounds that have higher boiling points than the polyfluorinated aliphatic hydrocarbon selected from the group consisting of chlorine, potassium permanganate, osmium tetroxide and ruthenium tetroxide; and
   3) separating a substantially pure polyfluorinated aliphatic hydrocarbon.

2. The process according to claim 1 wherein said dehydrohalogenating agents is selected from the group consisting of potassium hydroxide, sodium hydroxide, 1,5-diazabicyclo [3.4.0. ]nonene-5 and 1,8-diazabicyclo[5.4.0. ] undecene-7.

3. The process according to claim 1 wherein said oxidizing agent is potassium permanganate, osmium tetroxide, or ruthenium tetroxide.

4. The process according to claim 1 wherein said chlorinating agent is chlorine.

5. A process for producing substantially pure 1,1,1,3,3-pentafluoropropane from a crude reaction solution thereof containing unsaturated as well as unsaturated and saturated halogenated hydrocarbon impurities, said process comprising the steps of
   1) treating said reaction solution with a dehydrohalogenating agent selected from the group consisting of an alkali metal hydroxide and bicyclic amidine at a temperature of from at about 0° to about 100° C. and using a molar ration of about 1:1 to about 1:5 impurity concentration to dehydrohalogenating agent thereby converting said halogenated impurities into corresponding olefinic impurities,
   2) reacting the solution of Step 1 with an agent that transforms the olefins into compounds having a higher boiling point than 1,1,1,3,3-pentafluoropropane said agent selected from the group consisting of chlorine, potassium permanganate, osmium tetroxide and ruthenium tetroxide;

3) separating said 1,1,1,3,3-pentafluoropropane from the reaction mixture formed in Step 2 by distillation.

6. The process according to claim 5 wherein said alkali metal hydroxide is selected from the group consisting of potassium hydroxide and sodium hydroxide and about 2 to about 20% by weight of water based on the crude reaction solution and about 1 to about 5% of a phase transfer catalyst based on the concentration of dehydrohalogenating agent are added to the crude reaction solution.

7. The process according to claim 5 wherein said bicyclic amidine is selected from the group consisting of 1,5-diazabicyclo[3.4.0] nonene-5 and 1,8-diazabicyclo [5.4.0] undecene- 7.

8. The process according to claim 5 wherein said oxidizing agent is selected from the group consisting of potassium permanganate, osmium tetroxide and ruthenium tetroxide and from about 2 to about 20% by weight of water based on the weight of 1,1,1,3,3-pentafluoropropane and about 0.1 to about 5 molar % based on the concentration of oxidizing agent is added to the solution formed in Step 1.

9. The process according to claim 5 wherein said chlorinating agent is chlorine, said chlorine being added to said the solution formed in Step 1 at a molar ratio of from about 1:1 to about 1.5:1 based on the concentration of olefinic impurities in the solution.

10. The process according to claim 9 wherein said solution to which chlorine has been added is irradiated with a mercury lamp having sufficient wattage so as to transform the olefinic impurities into their corresponding photochlorinated products.

\* \* \* \* \*